(12) United States Patent
Palovich et al.

(10) Patent No.: US 6,566,387 B1
(45) Date of Patent: May 20, 2003

(54) IL-8 RECEPTOR ANTAGONISTS

(75) Inventors: Michael R. Palovich, Norristown, PA (US); Katherine L. Widdowson, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/009,212

(22) PCT Filed: May 26, 2000

(86) PCT No.: PCT/US00/14661

§ 371 (c)(1),
(2), (4) Date: Nov. 8, 2001

(87) PCT Pub. No.: WO00/72845

PCT Pub. Date: Dec. 7, 2000

Related U.S. Application Data

(60) Provisional application No. 60/136,717, filed on May 28, 1999.

(51) Int. Cl.$^7$ ................ A61K 31/4152; A61K 31/4168; C07D 233/32; C07D 233/50
(52) U.S. Cl. ................... 514/401; 548/333.1; 548/331.1
(58) Field of Search .......................... 514/401; 548/307, 548/331.1, 333.1

(56) References Cited

FOREIGN PATENT DOCUMENTS

| WO | WO 98 06262 | 2/1998 |
|---|---|---|
| WO | WO 98 06397 | 2/1998 |
| WO | WO 98 06398 | 2/1998 |
| WO | WO 98 06399 | 2/1998 |
| WO | WO 98 06701 | 2/1998 |
| WO | WO 98/32439 | 7/1998 |
| WO | WO00/35442 | 6/2000 |

*Primary Examiner*—Phyllis G. Spivack
(74) *Attorney, Agent, or Firm*—Soma G. Simon; Mary E. McCarthy; Charles M. Kinzig

(57) ABSTRACT

The invention relates to the use of guanidine compounds in the treatment of disease states mediated by the chemokine, Interleukin-8 (IL-8).

5 Claims, No Drawings

IL-8 RECEPTOR ANTAGONISTS

This is a 371 of International Application PCT/US00/14661, filed May 26, 2000, which claims benefit from Provisional Application No: 60/136,717, filed May 28, 1999.

FIELD OF THE INVENTION

This invention relates to a novel group of guanidine compounds, processes for the preparation thereof, the use thereof in treating IL-8, GROα, GROβ, GROγ, NAP-2, and ENA-78 mediated diseases and pharmaceutical compositions for use in such therapy.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

GROα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al, *J. Cell Physiology* 129, 375 (1986) and Chang et al, *J. Immunol* 148, 451 (1992). All of the chemokines of the α-family which possess the ELR motif directly preceding the CXC motif bind to the IL-8 B receptor.

IL-8, GROα, GROβ, GROγ, NAP-2 and ENA-78 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals. GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, GROα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis, Strieter et al, *Science* 258, 1798 (1992).

In vitro, IL-8, GROα, GROβ, GROγ, and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor, Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8RB, which has high affinity for IL-8 as well as for GRO-α, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present invention are represented by the structure

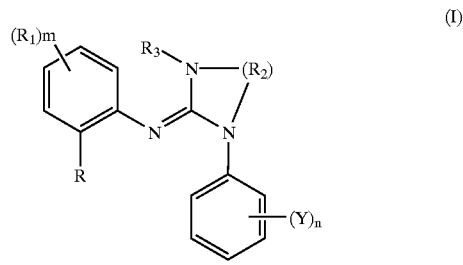

wherein:
R is OH, SH, NHSO$_2$R$_d$;

R$_d$ is NR$_6$R$_7$, alkyl, arylC1–4alklyl, arylC$_{2-4}$ alkenyl, heteroaryl, hetroaryl-C$_{1-4}$alkyl, heteroarylC$_{2-4}$ alkenyl, heterocyclic, heterocyclicC$_{1-4}$ alkyl, wherein the aryl, heteoaryl and heterocyclic rings may all be optionally substituted, R$_6$ and R$_7$ are independently hydrogen, or a C$_{1-4}$ alkyl group, or R$_6$ and R$_7$ together with the nitrogen to which they are attached form a 5 to 7 member ring which ring may optionally contain an additional heteroatom is selected from oxygen, nitrogen or sulfur, and which ring may be optionally substituted;

$R_1$ is independently selected from hydrogen; halogen; nitro; cyano; halosubstituted $C_{1-10}$ alkyl, $C_{1-10}$ alkyl, $C_{2-10}$ alkenyl, $C_{1-10}$ alkoxy, halosubstituted $C_{1-10}$ alkoxy, azide, $(CR_8R_8)_qS(O)_tR_4$, hydroxy, hydroxy $C_{1-4}$alkyl, aryl, aryl $C_{1-4}$ alkyl, aryloxy, aryl $C_{1-4}$ alkyloxy, heteroaryl, heteroarylalkyl, heterocyclic, heterocyclic $C_{1-4}$alkyl, heteroaryl $C_{1-4}$ alkyloxy, aryl $C_{2-10}$ alkenyl, heteroaryl $C_{2-10}$ alkenyl, heterocyclic $C_{2-10}$ alkenyl, $(CR_8R_8)_qNR_4R_5$, $C_{2-10}$ alkenyl $C(O)NR_4R_5$, $(CR_8R_8)_qC(O)NR_4R_5$, $(CR_8R_8)_qC(O)NR_4R_{10}$, $S(O)_3H$, $S(O)_3R_8$, $(CR_8R_8)_qC(O)R_{11}$, $C_{2-10}$ alkenyl $C(O)R_{11}$, $C_{2-10}$ alkenyl $C(O)OR_{11}(CR_8R_8)_qC(O)OR_{12}$, $(CR_8R_8)_qOC(O)R_{11}$, $(CR_8R_8)_qNR_4C(O)R_{11}$, $(CR_8R_8)_qNHS(O)_2R_{17}$, $(CR_8R_8)_qS(O)_2NR_4R_5$, or two $R_1$ moieties together may form $O-(CH_2)_sO-$ or a 5 to 6 membered unsaturated ring;

$R_2$ is independently selected from $C_{2-5}$alkyl and $C_{2-5}$alkenyl all of which moieties may be optionally substituted one to three times independently by halogen; nitro; halosubstituted $C_{1-4}$ alkyl; $C_{1-4}$ alkyl; amino, mono or di-$C_{1-4}$ alkyl substituted amine; hydroxy; $C_{1-4}$ alkoxy; $NR_9C(O)R_a$; $S(O)_mR_a$; $C(O)NR_6R_7$; $C(O)OH$; $C(O)OR_a$; $S(O)_2NR_6R_7$; $NHS(O)_2R_a$; and optionally containing, in addition to carbon, independently, 1 to 3 $NR_9$, O, C(O), S, SO, or $SO_2$ moities.

$R_3$ is independently selected from $C_{1-10}$ alkyl; halosubstituted $C_{1-10}$ alkyl; $C_{2-10}$ alkenyl; $C_{1-10}$ alkoxy; halosubstituted $C_{1-10}$alkoxy; azide; $S(O)_tR_4$; $(CR_8R_8)_q$ $S(O)_tR_4$; hydroxy; hydroxy substituted $C_{1-4}$alkyl; aryl; aryl $C_{1-4}$ alkyl; aryl $C_{2-10}$ alkenyl; aryloxy; aryl $C_{1-4}$ alkyloxy; heteroaryl; heteroarylalkyl; heteroaryl $C_{2-10}$ alkenyl; heteroaryl $C_{1-4}$ alkyloxy; heterocyclic, heterocyclic $C_{1-4}$alkyl; heterocyclic$C_{1-4}$alkyloxy; heterocyclic$C_{2-10}$ alkenyl; $(CR_8R_8)_qNR_4R_5$; $(CR_8R_8)_qC(O)NR_4R_5$; $C_{2-10}$ alkenyl $C(O)NR_4R_5$; $(CR_8R_8)_qC(O)NR_4R_{10}$; $S(O)_3R_8$; $(CR_8R_8)_qC(O)R_{11}$; $C_{2-10}$ alkenyl $C(O)R_{11}$; $C_{2-10}$ alkenyl $C(O)OR_{11}$; $(CR_8R_8)_qC(O)OR_{11}$; $(CR_8R_8)_qOC(O)R_{11}$; $(CR_8R_8)_qNR_4C(O)R_{11}$; $(CR_8R_8)_qC(NR_4)NR_4R_5$; $(CR_8R_8)_qNR_4C(NR_5)R_{11}$; $(CR_8R_8)_qNHS(O)_2R_{12}$; $(CR_8R_8)_qS(O)_2NR_4R_5$; or two $R_1$ moieties together may form $O-(CH_2)_sO$ or a 5 to 6 membered saturated or unsaturated ring, and wherein the alkyl, aryl, arylalkyl, heteroaryl, heterocyclic moieties may be optionally substituted;

q is 0, or an integer having a value of 1 to 10;

t is 0, or an integer having a value of 1 or 2;

s is an integer having a value of 1 to 3;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from oxygen, nitrogen or sulfur;

Y is independently selected from hydrogen; halogen; nitro; cyano; halosubstituted $C_{1-10}$ alkyl, $C_{1-10}$ alkyl, $C_{2-10}$ alkenyl, $C_{1-10}$ alkoxy, halosubstituted $C_{1-10}$ alkoxy, azide, $(CR_8R_8)_qS(O)_tR_4$, hydroxy, hydroxy$C_{1-4}$alkyl, aryl, aryl $C_{1-4}$ alkyl, aryloxy, aryl$C_{1-4}$ alkyloxy, heteroaryl, heteroarylalkyl, heteroaryl $C_{1-4}$ alkyloxy; heterocyclic, heterocyclic $C_{1-4}$alkyl, aryl $C_{2-10}$ alkenyl, heteroaryl $C_{2-10}$ alkenyl, heterocyclic $C_{2-10}$ alkenyl, $(CR_8R_8)_qNR_4R_5$, $C_{2-10}$ alkenyl $C(O)NR_4R_5$, $(CR_8R_8)_qC(O)NR_4R_5$, $(CR_8R_8)_qC(O)NR_4R_{10}$, $S(O)_3H$, $S(O)_3R_8$, $(CR_8R_8)_qC(O)R_{11}$, $C_{2-10}$ alkenyl $C(O)R_{11}$, $C_{2-10}$ alkenyl $C(O)OR_{11}$, $C(O)R_{11}$, $(CR_8R_8)_qC(O)OR_{12}$, $(CR_8R_8)_qOC(O)R_{11}$, $(CR_8R_8)_qNR_4C(O)R_{11}$, $(CR_8R_8)_qNHS(O)_2R_d$, $(CR_8R_8)_qS(O)_2NR_4R_5$, or two Y moieties together may form $O-(CH_2)_sO-$ or a 5 to 6 membered unsaturated ring, n is an integer having a value of 1 to 3, m is an integer having a value of 1 to 3, $R_8$ is hydrogen or $C_{1-4}$ alkyl, $R_9$ is hydrogen or a $C_{1-4}$ alkyl, $R_{10}$ is $C_{1-10}$ alkyl $C(O)_2R_8$, $R_{11}$ is hydrogen, $C_{1-4}$ alkyl, optionally substituted aryl, optionally substituted aryl $C_{1-4}$alkyl, optionally substituted heteroaryl, optionally substituted heteroaryl $C_{1-4}$alkyl, optionally substituted heterocyclic, or optionally substituted heterocyclic$C_{1-4}$alkyl, $R_{12}$ is hydrogen, $C_{1-10}$ alkyl, optionally substituted aryl or optionally substituted arylalkyl;

$R_{17}$ is $C_{1-4}$alkyl, aryl, arylalkyl, heteroaryl, heteroaryl $C_{1-4}$alkyl, heterocyclic, or heterocyclic$C_{1-4}$alkyl, wherein the aryl, heteroaryl and heterocyclic rings may all be optionally substituted; and $R_a$ is an alkyl, aryl, aryl$C_{1-4}$alkyl, heteroaryl, heteroaryl $C_{1-4}$alkyl, heterocyclic, or a heterocyclic $C_{1-4}$alkyl moiety, all of which moieties may be optionally substituted.

DETAILED DESCRIPTION OF THE INVENTION

The compounds of Formula (I) may also be used in association with the veterinary treatment of mammals, other than humans, in need of inhibition of IL-8 or other chemokines which bind to the IL-8RA and RB receptors. Chemokine mediated diseases for treatment, therapeutically or prophylactically, in animals include disease states such as those noted herein in the Methods of Treatment section.

Preferred compounds useful in the present invention include:

4-[[3-(2-bromophenyl)-4-oxo-1-(phenylmethyl)-2-imidazolidinylidene]imino]-3-hydroxybenzonitrile;

4-[[(7aS)-2-(2-bromophenyl)-hexahydro-1-oxo-3H-pyrrolo[1,2-c]imidazol-3-ylidene]amino]-3-hydroxybenzonitrile;

4-[[5-(2-bromophenyl)-3,3a,4,5-tetrahydro-1,1-dioxido-4-oxoimidazo[1,5-b]isothiazol-6(2H)-ylidene]amino]-3-hydroxybenzonitrile;

4-[[(6R,7aS)-2-(2-bromophenyl)-hexahydro-6-hydroxy-1-oxo-3H-pyrrolo[1,2-c]imidazol-3-ylidene]amino]-3-hydroxybenzonitrile;

4-[[(7aR)-2-(2-bromophenyl)-hexahydro-1-oxo-3H-pyrrolo[1,2-c]imidazol-3-ylidene]amino]-3-hydroxybenzonitrile, 4-[(S)-2-(2,3-Dichloro-phenyl)-1-oxo-hexahydro-pyrrolo[1,2-c]imidazol-3-ylideneamino]-3-hydroxy-benzonitrile, 4-[(R)-2-(2,3-Dichloro-phenyl)-1-oxo-hexahydro-pyrrolo[1,2-c]imidazol-3-ylideneamino]-3-hydroxy-benzonitrile, 4-[2-(2,3-Dichloro-phenyl)-1-oxo-hexahydro-pyrrolo[1,2-c]imidazol-3-ylideneamino]-3-hydroxy-benzonitrile, 4-[(S)-2-(2-Bromo-phenyl)-1-oxo-hexahydro-pyrrolo[1,2-c]imidazol-3-ylideneamino]-3-hydroxy-benzonitrile, 4-[(R)-2-(2-Bromo-phenyl)-1-oxo-hexahydro-pyrrolo[1,2-c]imidazol-3-ylideneamino]-3-hydroxy-benzonitrile, 4-[2-(2-Bromo-phenyl)-1-oxo-hexahydro-pyrrolo[1,2-c]imidazol-3-ylideneamino]-3-hydroxy-benzonitrile, and 4-[[2-(2-bromophenyl)-1,5,6,7,8,8a-hexahydro-1-oxoimidazo[1,5-a]pyridin-3(2H)-ylidene]amino]-3-hydroxybenzonitrile; or a pharmaceutically acceptable salt thereof.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{2-5}$alkyl" or "alkyl"—both straight and branched chain moieties of 2 to 5 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "alkenyl" is used herein at all occurrences to mean straight or branched chain moieties of 2–10 carbon atoms, unless the chain length is limited thereto, including, but not limited to, ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited to, pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

METHODS OF PREPARATION

The compounds of Formula (I) may be obtained by applying synthetic procedures, some of which are illustrated in the Schemes below. The synthesis provided for in these Schemes is applicable for producing compounds of Formula (I) having a variety of different R, $R_1$, and aryl groups which are reacted, employing optional substituents which are suitably protected, to achieve compatibility with the reactions outlined herein. Subsequent deprotection, in those cases, then affords compounds of the nature generally disclosed. Once the guanidine nucleus has been established, further compounds of these formulas may be prepared by applying standard techniques for functional group interconversion, well known in the art. While the schemes are shown with compounds only of Formula (I) this is merely for illustration purposes only.

Scheme 1

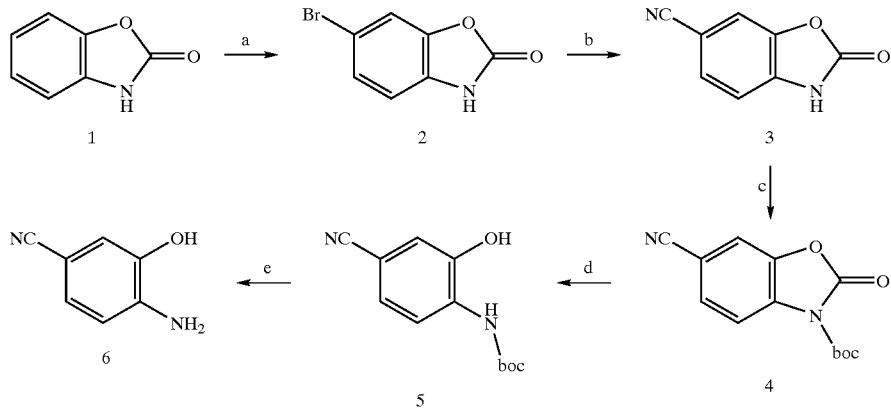

a) $Br_2$, NaOAc, HOAc; b) CuCN, DMF, reflux; c) $(BOC)_2O$, DMAP, TEA; d) $K_2CO_3$, MeOH; e) TFA The desired aniline 6-scheme-1 can be prepared from the commercially available benzoxazolinone 1-scheme-1. Bromide 2-scheme-1 can be prepared from benzoxazolinone 1-scheme-1 using standard bromination conditions such as bromine and sodium acetate in acetic acid. Bromide 2-scheme-1 can be converted to the cyanide 3-scheme-1 using standard procedures such as copper (I) cyanide in refluxing DMF. The amide 3-scheme-1 can be converted to the BOC protected compound 4-scheme-1 using standard conditions such as BOC anhydride and triethylamine with a catalytic amount of dimethylaminopyridine in methylene chloride or another suitable organic solvent. The oxazolinone 4-scheme-1 can be converted to the desired aniline 6-scheme-1 by first hydrolysis to the phenol 5-scheme-1 using standard conditions such as potassium carbonate in methanol followed by removal of the BOC protecting group using standard conditions such as trifluoroacetic acid in methylene chloride or another suitable organic solvent to give the aniline 6-scheme-1.

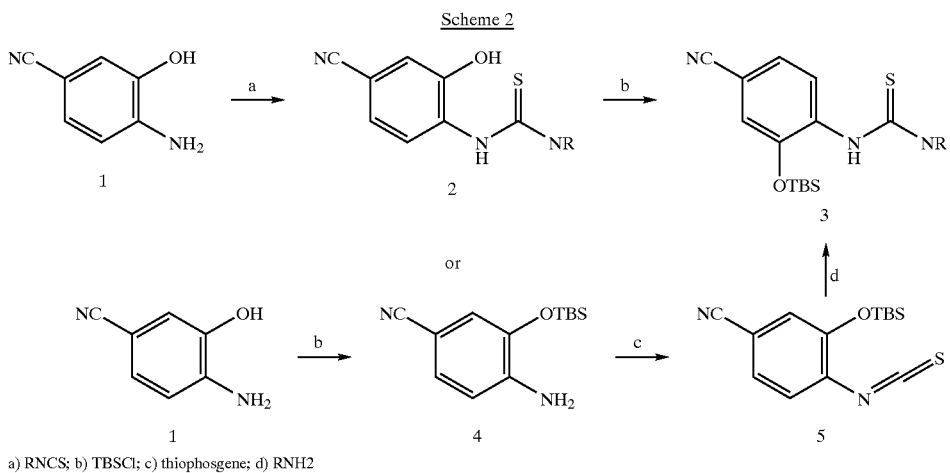

a) RNCS; b) TBSCl; c) thiophosgene; d) RNH2

The desired thiourea 3-scheme-2 can be prepared as outlined in scheme 2. The aniline 1-scheme-2 can be coupled with a commercially available isothiocyanate or with an isothiocyanate made from condensing a commercially available amine with thiophosgene or a thiophosgene equivalent to give the thiourea 2-scheme-2. The phenol 2-scheme-2 can be protected as the TBS ether 3-scheme-2 using standard conditions such as TBSCl and imidazole in THF or another suitable organic solvent. Alternatively the amine 1-scheme-2 can be converted to the isothiocyanate 5-Scheme-2 by first protecting the phenol 1-Scheme-2 with a suitable protecting group such as the TBS ether 4-scheme-2 using standard conditions such as TBSCl and an amine base such as imidazole in THF or another suitable organic solvent. The thiourea 5-scheme-2 can be made by condensing the amine 4-scheme 2 with thiophosgene in the presence of a base such as potassium carbonate. The desired thiourea 3-scheme-2 can be prepared from the isothiocyanate 5-scheme-2 by condensing it with the desired amine in a suitable organic solvent such as ethanol or DMF.

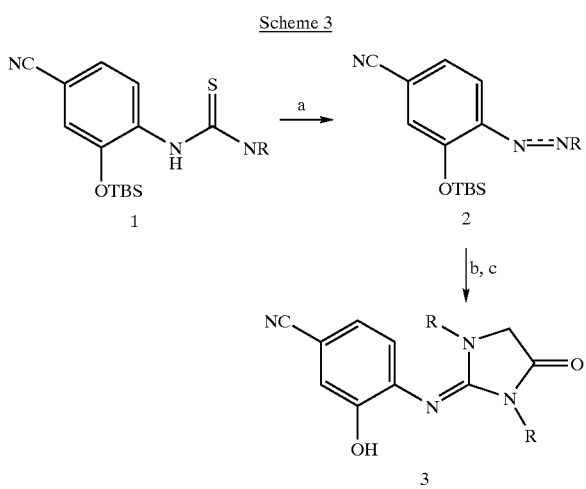

a) MsCl, TEA; b) aminoester, THF c) TBAF, THF

The desired lactam 3-scheme-3 can be prepared as outlined in Scheme 3. The carbodiimide 2-Scheme-3 can be prepared from the thiourea 1-scheme-3 using standard conditions such as an excess amount of methane sulfonyl chloride and a suitable amine base such as triethylamine in an organic solvent preferably methylene chloride at room temperature. The lactam 3-Scheme-3 can be prepared from the carbodiimide 2-Scheme-3 by first condensing the carbodiimide 2-Scheme-3 with the desired α-aminoester in a suitable organic solvent such as THF followed by removal of the TBS group using standard conditions such as TBAF in THF at 0° C.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Example 1

Preparation of 4-[[3-(2-Bromophenyl)-4-oxo-1-(Phenylmethyl)-2-imidazolidinylidene]imino]-3-hydroxybenzonitrile a) Preparation of 4-Bromo-1,2-benzoxazolinone.

To a solution of benzoxazolinone (10 g, 74 mmol) in acetic acid (50 mL) at 0° C. was added sodium acetate (7.4 g, 74 mmol) and bromine (3.8 mL, 74 mmol) and the reaction mixture was allowed to warm to rt. After 21 h, the precipitate was collected by filtration and washed with water. The filtrate was concentrated under reduced pressure to give more solid material which was collected by filtration followed by washing with water. The material was combined to give 14 g (88%) of 4-bromo-1,2-benzoxazolinone as a yellow solid which required no further purification. $^1$H NMR (400 MHz, DMSO) δ 7.6 (s, 1H), 7.3 (d, 1H), 7.0 (d, 1H); MS(EI) m/e 212 (M$^+$).

b) Preparation of 4-Cyano-1,2-benzoxazolinone.

To a solution of 4-bromo-1,2-benzoxazolinone (5.0 g, 23 mmol) in DMF (11 mL) was added copper (I) cyanide (3.6 g, 39 mmol) and the reaction heated at 165° C. After 6.5 h, the reaction mixture was cooled to rt and water (20 mL) and sodium cyanide (3.6 g) were added and the reaction heated at 100° C. After 12 h, the reaction mixture was extracted with ethyl acetate and the combined organic layers were filtered through a scrub pad of silica gel eluting with ethyl acetate. The filtrate was concentrated under reduced pressure to give 1.9 g (51%) of 4-cyano-1,2-benzoxazolinone as a brown solid which required no further purification. $^1$H NMR (400 MHz, DMSO) δ 7.8 (s, 1H), 7.6 (d, 1H), 7.2 (d, 1H).

c) Preparation of N-t-Butylacetoxy-4-cyano-1,2-benzoxazolinone.

To a solution of 4-cyano-1,2-benzoxazolinone (1.9 g, 15 mmol) in THF (50 mL) at 0° C. was added triethylamine (2.5 mL, 18 mmol), DMAP (0.37 g, 3.0 mmol) and BOC anhydride (4.3 g, 20 mmol) and the reaction mixture was allowed to warm to rt. After 1.5 h, the mixture was quenched with water (100 mL) and extracted with ethyl acetate. The combined organic layers were washed with brine, dried over anhydrous magnesium sulfate and concentrated under reduced pressure to give 4.3 g (100%) of N-t-butylacetoxy-4-cyano-1,2-benzoxazolinone as a yellow solid which required no further purification. $^1$H NMR (400 MHz, CDCl$_3$) δ 7.8 (d, 1H), 7.55 (d, 1H), 7.45 (s, 1H), 1.65 (s, 9H).

d) Preparation of N-t-Butylacetoxy-4-cyano-2-hydroxyl Aniline.

To a solution of N-t-butylacetoxy-4-cyano-1,2-benzoxazolinone (4.3 g, 16 mmol) in methanol (50 mL) was added potassium carbonate (2.3 g, 16 mmol). After 1.5 h, the reaction was quenched with water (100 mL) and extracted with ethyl acetate. The combined organic layers were washed with brine, dried over anhydrous magnesium sulfate and concentrated under reduced pressure to give 3.1 g (81%) of N-t-butylacetoxy4-cyano-2-hydroxyl aniline as a brown foam which required no further purification. $^1$H NMR (400 MHz, CDCl$_3$) δ 7.7 (d, 1H), 7.15 (s, 1H), 7.1 (d, 1H), 1.5 (s, 9H).

e) Preparation of 4-Cyano-2-hydroxyl Aniline.

To a solution of N-t-butylacetoxy-4-cyano-2-hydroxyl aniline (3.1 g, 13 mmol) in methylene chloride (100 mL) at 0° C. was added trifluoroacetic acid and the reaction mixture was allowed to warm to rt. After 2.5 h, the reaction was quenched with water (100 mL) and extracted with ethyl acetate. The combined organic layers were washed with brine, dried over anhydrous magnesium sulfate and concentrated under reduced pressure. The crude material was purified by flash column chromatography (50% ethyl acetate/hexanes) to give 1.7 g (96%) of 4-cyano-2-hydroxyl aniline as a tan solid. $^1$H NMR (400 MHz, DMSO) δ 7.0 (d, 1H), 6.85 (s, 1H), 6.65 (d, 1H); MS(EI) m/e 134 (M$^+$).

f) Preparation of N-(4-Cyano-2-hydroxyphenyl)-N'-(2-bromophenyl)thiourea.

To a solution of 4-cyano-2-hydroxyl aniline (1.0 g, 7.5 mmol) in ethanol (20 mL) was added 2-bromophenylisothiocyanate (1.0 mL, 7.5 mmol). After 24 h, the reaction mixture was concentrated under reduced pressure to give 2.0 g (77%) of N-(4-cyano-2-hydroxyphenyl)-N'-(2-bromophenyl) thiourea as a yellow solid which required no further purification. $^1$H NMR (400 MHz, DMSO) δ 10.8 (s, 1H), 10.1 (s, 1H), 9.6 (s, 1H), 8.7 (d, 1H), 7.7 (d, 1H), 7.6 (d, 1H), 7.4 (t, 1H), 7.25 (d, 1H and d, 2H); MS(EI) m/e 229 (100), 348 (75 (M$^+$)), 462 (30), 695 (10).

g) Preparation of N-(4-Cyano-2-t-butyldimethylsilanoxyphenyl)-N'-(2-bromophenyl)thio Urea.

To a solution of N-(4-cyano-2-hydroxyphenyl)-N'-(2-bromophenyl)thio urea (3.5 g, 10 mmol) in THF (50 mL) at 0° C. was added imidazole (1.0 g, 15 mmol) and TBSCl (1.5 g, 10 mmol). After 1 h, the reaction mixture quenched with water (100 mL) and extracted with ethyl acetate. The combined organic layers were washed with brine, dried over anhydrous magnesium sulfate and concentrated under reduced pressure. The crude material was crystallized from ethyl acetate to give 3.9 g (84%) of N-(4-cyano-2-t-butyldimethylsilanoxyphenyl)-N'-(2-bromophenyl)thio urea as a yellow solid. $^1$H NMR (400 MHz, DMSO) δ 9.9 (s, 1H), 9.2 (s, 1H), 8.1 (d, 1H), 7.7 (d, 1H), 7.6 (d, 1H), 7.45 (d, 1H), 7.4 (t, 1H), 7.35 (s, 1H), 7.2 (t, 1H); MS(EI) m/e 347 (100 (M$^+$)), 175 (40), 461 (40).

h) Preparation of N-(4-Cyano-2-t-butyldimethylsilanoxyphenyl)-N'-(2-bromophenyl) carbodiimide.

To a solution of N-(4-cyano-2-t-butyldimethylsilanoxyphenyl)-N'-(2-bromophenyl)thio urea (3.4 g, 7.4 mmol) in methylene chloride (40 mL) at 0° C. was added triethylamine (3.1 mL, 22 mmol), DMAP (20 mg) and methane sulfonyl chloride (1.1 mL, 15 mmol). After 25 min, the reaction mixture was quenched with water (100 mL) and extracted with ethyl acetate. The combined organic layers were washed with brine, dried over anhydrous magnesium sulfate and concentrated under reduced pressure to give 3.3 g (100%) of N-(4-cyano-2-t-butyldimethylsilanoxyphenyl)-N'-(2-bromophenyl) carbodiimide as a yellow solid which required no further purification. $^1$H NMR (400 MHz, DMSO) δ 7.7 (d, 1H), 7.45 (d, 1H), 7.4 (m, 4H), 7.15 (t, 1H).

i) Standard Procedure for the Synthesis of Cyclic Tetralkylguanidines. Preparation of 4-[[3-(2-Bromophenyl)-4-oxo-1-(phenylmethyl)-2-imidazolidinylidene]imino]-3-hydroxybenzonitrile.

To a solution of N-(4-cyano-2-t-butyldimethylsilanoxyphenyl)-N'-(2-bromophenyl) carbodiimide (86 mg, 0.20 mmol) in THF (2 mL) was added diisopropylethylamine (25 μL, 0.57 mmol) and N-benzyl glycine ethyl ester (41 mg, 0.22 mmol). After 15 min, to the mixture was added methanol (0.1 mL) and then TBAF (0.24 mL, 0.24 mmol) at 0° C. After 30 min, the reaction mixture was quenched with water (2 mL) and extraced with ethyl acetate. The combined organic layers were washed with brine, dried over anhydrous magnesium sulfate and concentrated under reduced pressure. The crude material was purified by recrystallization (methylene chloride/hexanes) to give 74.5 mg (80%) of 4-[[3-(2-bromophenyl)-4-oxo-1-(phenylmethyl)-2-imidazolidinylidene]imino]-3-hydroxybenzonitrile as a tan powder. $^1$H NMR (400 MHz, MeOD) δ 7.45 (2H, d), 7.35 (2H, t), 7.3 (1H, d), 7.25 (1H, d), 7.15 (1H, d), 6.9 (3H, m), 6.8 (1H, d), 6.6 (1H, t), 4.6 (2H, m), 4.0 (2H, s); MS(EI) m/e 463 (100 (M$^+$)).

j) Preparation of 4-[[(7aS)-2-(2-Bromophenyl)-hexahydro-1-oxo-3H-pyrrolo[1,2-c]imidazol-3-ylidene]amino]-3-hydroxybenzonitrile.

The standard procedure was followed using N-(4-cyano-2-t-butyldimethylsilanoxyphenyl)-N'-(2-bromophenyl) carbodiimide (54 mg, 0.13 mmol), diisopropylethylamine (32 μL, 0.29 mmol), L-proline benzylester hydro chloride (34 mg, 0.14 mmol) and TBAF (0.16 mL, 0.16 mmol) in THF (2 mL) and methanol (0.1 mL) to give 36 mg (67%) of 4-[[(7aS)-2-(2-bromophenyl)-hexahydro-1-oxo-3H-pyrrolo[1,2-c]imidazol-3-ylidene]amino]-3-hydroxybenzonitrile as a tan powder. $^1$H NMR (400 MHz, MeOD) δ 7.6 (2H, m), 7.35 (3H, m), 7.15 (1H, m), 7.0 (1H, m), 4.5 (1H, t), 3.0 (1H, m), 2.4 (1H, m), 2.2 (1H, m), 2.05 (2H, m); MS(EI) m/e 412 (M$^+$).

k) Preparation of 4-[[5-(2-Bromophenyl)-3,3a,4,5-tetrahydro-1,1-dioxido-4-oxoimidazo[1,5-b]isothiazol-6 (2H)-ylidene]amino]-3-hydroxybenzonitrile.

The standard procedure was followed using N-(4-cyano-2-t-butyldimethylsilanoxyphenyl)-N'-(2-bromophenyl) carbodiimide (60 mg, 0.14 mmol), diisopropylethylamine (17 μL, 0.15 mmol), aminoester (27 mg, 0.15 mmol) and TBAF (0.17 mL, 0.15 mmol) in THF (1.5 mL) and methanol (0.1 mL) to give 46 mg (71%) of 4-[[5-(2-bromophenyl)-3,3a,4,5-tetrahydro-1,1-dioxido-4-oxoimidazo[1,5-b]isothiazol-6(2H)-ylidene]amino]-3-hydroxybenzonitrile as a tan powder. $^1$H NMR (400 MHz, MeOD) δ 8.1 (1H, d), 7.8 (1H, s), 7.75 (1H, d), 7.7 (1H, d), 7.6 (2H, m), 7.25 (1H, t), 4.35 (1H, t), 3.9 (2H, s), 3.25 (1H, t), 2.9 (1H, m), 2.7 (1H, m); MS(EI) m/e 330 (100), 662 (20).

l) Preparation of 4-[[(6R,7aS)-2-(2-Bromophenyl)-hexahydro-6-hydroxy-1-oxo-3H-pyrrolo[1,2-c]imidazol-3-ylidene]amino]-3-hydroxybenzonitrile.

The standard procedure was followed using N-(4-cyano-2-t-butyldimethylsilanoxyphenyl)-N'-(2-bromophenyl) carbodiimide (102 mg, 0.24 mmol), diisopropylethylamine (60 μL, 0.26 mmol), hydroxy L-proline methyl ester hydro chloride (44 mg, 0.26 mmol) and TBAF (0.29 mL, 0.29 mmol) in THF (2.5 mL) and methanol (0.1 mL) to give 80 mg (78%) of 4-[[(6R,7aS)-2-(2-bromophenyl)-hexahydro-6-hydroxy-1-oxo-3H-pyrrolo[1,2-c]imidazol-3-ylidene]amino]-3-hydroxybenzonitrile as a tan powder. MS(EI) m/e 427 (100 (M$^+$)).

m) Preparation of 4-[[(7aR)-2-(2-Bromophenyl)-hexahydro-1-oxo-3H-pyrrolo[1,2-c]imidazol-3-ylidene]amino]-3-hydroxybenzonitrile.

The standard procedure was followed using N-(4-cyano-2-t-butyldimethylsilanoxyphenyl)-N'-(2-bromophenyl) carbodiimide (107 mg, 0.25 mmol), diisopropylethylamine (71 μL, 0.55 mmol), D-proline methyl ester hydro chloride (46 mg, 0.28 mmol) and TBAF (0.30 mL, 0.30 mmol) in THF (2.5 mL) and methanol (0.1 mL) to give 80 mg (78%) of 4-[[(7aR)-2-(2-bromophenyl)-hexahydro-1-oxo-3H-pyrrolo[1,2-c]imidazol-3-ylidene]amino]-3-hydroxybenzonitrile as a tan powder. MS(EI) m/e 411 (100(M$^+$)).

n) Preparation of 4-[[2-(2-Bromophenyl)-1,5,6,7,8,8a-hexahydro-1-oxoimidazo[1,5-a]pyridin-3(2H)-ylidene]amino]-3-hydroxybenzonitrile.

The standard procedure was followed using N-(4-cyano-2-t-butyldimethylsilanoxyphenyl)-N'-(2-bromophenyl) carbodiimide (106 mg, 0.25 mmol), diisopropylethylamine (71 μL, 0.28 mmol), methyl pipecolinate hydro chloride (50 mg, 0.28 mmol) and TBAF (0.30 mL, 0.30 mmol) in THF (2.5 mL) and methanol (0.1 mL) to give 80 mg (75%) of 4-[[2-(2-bromophenyl)-1,5,6,7,8,8a-hexahydro-1-oxoimidazo[1,5-a]pyridin-3(2H)-ylidene]amino]-3-hydroxybenzonitrile as a tan powder. MS (EI) m/e 425 (100(M$^+$)).

Method of Treatment

The compounds of Formula (I) or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8α or β receptor, also referred to as the type I or type II receptor.

Accordingly, the present invention provides a method of treating a chemokine mediated disease, wherein the chemokine is one which binds to an IL-8α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

For purposes herein, the compounds of Formula (I) and (II) all have the same dosages, and formulations as that of Formula (I) are used interchangeably.

The compounds of Formula (I) are admninistered in an amount sufficient to inhibit cytokine function, in particular IL-8, GROα, GROβ, GROγ, NAP-2 or ENA-78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence IL-8, GROα, GROβ, GROγ, NAP-2 or ENA-78 above basal levels in cells or tissues in IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis, atherosclerosis, osteoporosis, gingivitis and undesired hematopoietic stem cells release.

These diseases are primarily characterized by massive neutrophil infiltration, T-cell infiltration, or neovascular growth, and are associated with increased IL-8, GROα, GROβ, GROγ or NAP-2 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ or NAP-2 has the unique property of promoting neutrophil chemotaxis, enzyme release including but not limited to elastase release as well as superoxide production and activation. The α-chemokines but particularly, GROα, GROβ, GROγ or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., *Nature* 381, pp 661 (1996) and Koup et al., *Nature* 381, pp 667 (1996).

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., *Stroke*, Vol. 25., No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

The compounds of Formula (I) are administered in an amount sufficient to inhibit binding to the IL-8 alpha or beta receptors such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown, in some instances, to be dual inhibitors of both recombinant type I and type II IL-8 receptors. Preferably the compounds are inhibitors of only one receptor, more preferably Type II.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8α or β receptor plays a role, such as but not limited IL-8, GROα, GROβ, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to, IL-8, GRO-α, GRO-β, GRO-γ, NAP-2, ENA-78, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

Biological Examples

The IL-8, and Gro-α chemokine inhibitiory effects of compounds of the present invention were determined by the following in vitro assay:

Receptor Binding Assays:

[$^{125}$I] IL-8 (human recombinant) was obtained from Amersham Corp., Arlington Heights, Ill., with specific activity 2000 Ci/mmol. Gro-α was obtained from NEN—New England Nuclear. All other chemicals were of analytical grade. High levels of recombinant human IL-8 type α and β receptors were individually expressed in Chinese hamster ovary cells as described previously (Holmes, et al., Science, 1991, 253, 1278). The Chinese hamster ovary membranes were homogenized according to a previously described protocol (Haour, et al., J Biol Chem., 249 pp 2195–2205 (1974)). Except that the homogenization buffer was changed to 10 mM Tris-HCL, 1 mM MgSO4, 0.5 mM EDTA (ethylene-diaminetetraacetic acid), 1 mMPMSF (α-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained $^{125}$I IL-8 (0.25 nM) or $^{125}$I Gro-α and 0.5 µg/mL of IL-8Rα or 1.0 µg/mL of IL-8Rβ membranes in 20 mM Bis-Trispropane and 0.4 mM Tris HCl buffers, pH 8.0, containing 1.2 mM $MgSO_4$, 0.1 mM EDTA, 25 mM NaCl and 0.03% CHAPS. In addition, drug or compound of interest was added which had been pre-dissolved in DMSO so as to reach a final concentration of between 0.01 nM and 100 uM. The assay was initiated by addition of $^{125}$I-IL-8. After 1 hour at room temperature the plate was harvested using a Tomtec 96-well harvester onto a glass fiber filtermat blocked with 1% polyethylenimine/ 0.5% BSA and washed 3 times with 25 mM NaCl, 10 mM TrisHCl, 1 mM $MgSO_4$, 0.5 mM EDTA, 0.03% CHAPS, pH 7.4. The filter was then dried and counted on the Betaplate liquid scintillation counter. The recombinant IL-8Rα, or Type I, receptor is also referred to herein as the non-permissive receptor and the recombinant IL-8Rβ, or Type II, receptor is referred to as the permissive receptor.

All of the exemplified compounds of Formulas (I) noted herein in the Synthetic Chemistry Section, Example 1 to 15, demonstrated an $IC_{50}$ from about 45 to about <1 µg/mL in the permissive models for IL-8 receptor inhibition. Of those compounds tested, Examples 1 to 12 were also found to be inhibitors of Gro-α binding at about the same level.

Chemotaxis Assay:

The in vitro inhibitory properties of these compounds are determined in the neutrophil chemotaxis assay as described in Current Protocols in Immunology, vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 are placed in the bottom chamber of a 48 multiwell chamber (Neuro Probe, Cabin John, MD) at a concentration between 0.1 and 100 nM. The two chambers are separated by a 5 um polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% $CO_2$. At the end of the incubation period, the polycarbonate membrane is removed and the top side washed, the membrane then stained using the Diff Quick staining protocol (Baxter Products, McGaw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay:

The compounds of this invention are tested for their ability to prevent Elastase release from human neutrophils. Neutrophils are isolated from human blood as described in Current Protocols in Immunology Vol I, Suppl 1 Unit 7.23.1. PMNs 0.88×$10^6$ cells suspended in Ringer's Solution (NaCl 118, KCl 4.56, $NaHCO_3$ 25, $KH_2PO_4$ 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800×g 5 min) and 100 ul of the supernatant removed. This suppernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al J. Biol Chem 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specfic brain regions which follow experimentally induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA was isolated and Northern blot hybridization is performed and quantitated relative to an TNF-α positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (46±8%, p<0.05), LC (30±3%, p<0.01) and LA (32±3%, p<0.01) at 6 hr. which resolves by 24 hr. following injury. In the contralateral hemisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury Model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

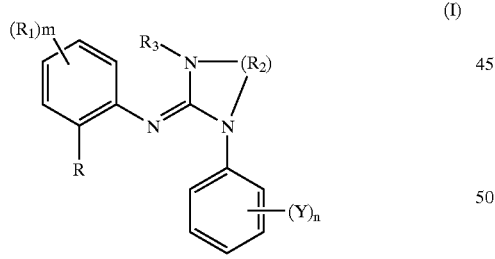

(I)

wherein:

R is OH, SH, NHSO$_2$R$_d$;

R$_d$ is NR$_6$R$_7$, alkyl, arylC$_{1-4}$alklyl, arylC$_{2-4}$ alkenyl, heteroaryl, hetroarylC$_{1-4}$alkyl, heteroarylC$_{2-4}$ alkenyl, heterocyclic, heterocyclicC$_{1-4}$ alkyl;

R$_6$ and R$_7$ are independently hydrogen, or a C$_{1-4}$ alkyl group, or R$_6$ and R$_7$ together with the nitrogen to which they are attached form a 5- to 7-membered ring, which ring may optionally contain an additional heteroatom, selected from oxygen, nitrogen or sulfur;

R$_1$ is independently selected from hydrogen; halogen; nitro; cyano; halosubstituted C$_{1-10}$ alkyl, C$_{1-10}$ alkyl, C$_{2-10}$ alkenyl, C$_{1-10}$ alkoxy, halosubstituted C$_{1-10}$ alkoxy, azide, (CR$_8$R$_8$)$_q$S(O)$_t$R$_4$, hydroxy, hydroxy C$_{1-4}$alkyl, aryl, aryl C$_{1-4}$ alkyl, aryloxy, aryl C$_{1-4}$ alkyloxy, heteroaryl, heteroarylalkyl, heterocyclic, heterocyclic C$_{1-4}$alkyl, heteroaryl C$_{1-4}$ alkyloxy, aryl C$_{2-10}$ alkenyl, heteroaryl C$_{2-10}$ alkenyl, heterocyclic C$_{2-10}$ alkenyl, (CR$_8$R$_8$)$_q$NR$_4$R$_5$, C$_{2-10}$ alkenyl C(O)NR$_4$R$_5$, (CR$_8$R$_8$)$_q$C(O)NR$_4$R$_5$, (CR$_8$R$_8$)$_q$C(O)NR$_4$R$_{10}$, S(O)$_3$H, S(O)$_3$R$_8$, (CR$_8$R$_8$)$_q$C(O)R$_{11}$, C$_{2-10}$ alkenyl C(O)R$_{11}$, C$_{2-10}$ alkenyl C(O)OR$_{11}$(CR$_8$R$_8$)$_q$C(O)OR$_{12}$, (CR$_8$R$_8$)$_q$OC(O)R$_{11}$, (CR$_8$R$_8$)$_q$NR$_4$C(O)R$_{11}$, (CR$_8$R$_8$)$_q$NHS(O)$_2$R$_{17}$, (CR$_8$R$_8$)$_q$S(O)$_2$NR$_4$R$_5$;

R$_2$ is independently selected from C$_{2-5}$alkyl and C$_{2-5}$alkenyl, all of which moieties may be optionally substituted one to three times independently by halogen, nitro, halosubstituted C$_{1-4}$ alkyl, C$_{1-4}$ alkyl, amino, mono- or di-C$_{1-4}$ alkyl substituted amine, hydroxy, C$_{1-4}$ alkoxy, NR$_9$C(O)R$_a$, S(O)$_m$R$_a$, C(O) NR$_6$R$_7$, C(O)OH, C(O)OR$_a$, S(O)$_2$NR$_6$R$_7$, NHS(O)$_2$R$_a$;

R$_3$ is independently selected from C$_{1-10}$ alkyl, halosubstituted C$_{1-10}$ alkyl, C$_{2-10}$ alkenyl, C$_{1-10}$ alkoxy, halosubstituted C$_{1-10}$alkoxy, azide, S(O)$_t$ R$_4$, (CR$_8$R$_8$)$_q$ S(O)$_t$R$_4$, hydroxy, hydroxy substituted C$_{1-4}$alkyl, aryl, aryl C$_{1-4}$ alkyl, aryl C$_{2-10}$ alkenyl, aryloxy, aryl C$_{1-4}$ alkyloxy, heteroaryl, heteroarylalkyl, heteroaryl C$_{2-10}$ alkenyl, heteroaryl C$_{1-4}$ alkyloxy, heterocyclic, heterocyclic C$_{1-4}$alkyl, heterocyclicC$_{1-4}$alkyloxy, heterocyclicC$_{2-10}$ alkenyl, (CR$_8$R$_8$)$_q$NR$_4$R$_5$, (CR$_8$R$_8$)$_q$C(O)NR$_4$R$_5$, C$_{2-10}$ alkenyl C(O)NR$_4$R$_5$, (CR$_8$R$_8$)$_q$C(O)NR$_4$R$_{10}$, S(O)$_3$R$_8$, (CR$_8$R$_8$)$_q$C(O)R$_{11}$, C$_{2-10}$ alkenyl C(O)R$_{11}$, C$_{2-10}$ alkenyl C(O)OR$_{11}$, (CR$_8$R$_8$)$_q$C(O)OR$_{11}$, (CR$_8$R$_8$)$_q$OC(O)R$_{11}$, (CR$_8$R$_8$)$_q$NR$_4$C(O)R$_{11}$, (CR$_8$R$_8$)$_q$C(NR$_4$)NR$_4$R$_5$, (CR$_8$R$_8$)$_q$NR$_4$C(NR$_5$)R$_{11}$, (CR$_8$R$_8$)$_q$NHS(O)$_2$R$_{12}$, (CR$_8$R$_8$)$_q$S(O)$_2$NR$_4$R$_5$;

q is 0, or an integer of 1 to 10;

t is 0, or an integer of 1 or 2;

s is an integer of 1 to 3;

R$_4$ and R$_5$ are independently hydrogen, C$_{1-4}$ alkyl, aryl, aryl C$_{1-4}$alkyl, heteroaryl, heteroaryl C$_{1-4}$alkyl, heterocyclic, heterocyclicC$_{1-4}$ alkyl, or R$_4$ and R$_5$ together with the nitrogen to which they are attached form a 5 to 7-membered ring which may optionally comprise an additional heteroatom selected from oxygen, nitrogen or sulfur, Y is independently selected from hydrogen, halogen, nitro, cyano, halosubstituted C$_{1-10}$ alkyl, C$_{1-10}$ alkyl, C$_{2-10}$ alkenyl, C$_{1-10}$ alkoxy, halosubstituted C$_{1-10}$ alkoxy, azide, (CR$_8$R$_8$)$_q$S(O)$_t$R$_4$, hydroxy, hydroxy C$_{1-4}$alkyl, aryl, aryl C$_{1-4}$ alkyl, aryloxy, arylC$_{1-4}$ alkyloxy, heteroaryl, heteroarylalkyl, heteroaryl C$_{1-4}$ alkyloxy, heterocyclic, heterocyclic C$_{1-4}$alkyl, aryl C$_{2-10}$ alkenyl, heteroaryl C$_{2-10}$ alkenyl, heterocyclic C$_{2-10}$ alkenyl, (CR$_8$R$_8$)$_q$NR$_4$R$_5$, C$_{2-10}$ alkenyl C(O) NR$_4$R$_5$, (CR$_8$R$_8$)$_q$C(O)NR$_4$R$_5$, (CR$_8$R$_8$)$_q$C(O)NR$_4$R$_{10}$, S(O)$_3$H, S(O)$_3$R$_8$, (CR$_8$R$_8$)$_q$C(O)R$_{11}$, C$_{2-10}$ alkenyl C(O)R$_{11}$, C$_{2-10}$ alkenyl C(O)OR$_{11}$, C(O)R$_{11}$, (CR$_8$R$_8$)$_q$C(O)OR$_{12}$, (CR$_8$R$_8$)$_q$OC(O)R$_{11}$, (CR$_8$R$_8$)$_q$NR$_4$C(O)R$_{11}$, (CR$_8$R$_8$)$_q$NHS(O)$_2$R$_d$, (CR$_8$R$_8$)$_q$S(O)$_2$NR$_4$R$_5$;

n is an integer of 1 to 3;

m is an integer of 1 to 3;

R$_8$ is hydrogen or C$_{1-4}$ alkyl;

R$_9$ is hydrogen or C$_{1-4}$ alkyl;

R$_{10}$ is C$_{1-10}$ alkyl C(O)$_2$R$_8$;

R$_{11}$ is hydrogen, C$_{1-4}$ alkyl, aryl, aryl C$_{1-4}$alkyl, heteroaryl, heteroarylC$_{1-4}$alkyl, heterocyclic or heterocyclicC$_{1-4}$alkyl;

$R_{12}$ is hydrogen, $C_{1-10}$ alkyl, aryl or arylalkyl;

$R_{17}$ is $C_{1-4}$alkyl, aryl, arylalkyl, heteroaryl, heteroaryl $C_{1-4}$alkyl, heterocyclic, or heterocyclic$C_{1-4}$alkyl; and $R_a$ is an alkyl, aryl, aryl$C_{1-4}$alkyl, heteroaryl, heteroaryl $C_{1-4}$alkyl, heterocyclic, or a heterocyclic $C_{1-4}$alkyl moiety.

2. The compound:

4-[[3-(2-bromophenyl)-4-oxo-1-(phenylmethyl)-2-imidazolidinylidene]amino]-3-hydroxybenzonitrile;

or a pharmaceutically acceptable salt thereof.

3. A pharmaceutical composition comprising an effective amount of a compound according to claim 1, and a pharmaceutically acceptable carrier or diluent.

4. A method of treating a chemokine mediated disease state, wherein the chemokine binds to an IL-8α or β receptor in a mammal, which comprises administering to said mammal an effective amount of a compound of the formula according to claim 1.

5. The method according to claim 4 wherein the mammal is afflicted with a chemokine mediated disease selected from psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, Alzheimers disease, allograft rejections, malaria, restenosis, angiogenesis, atherosclerosis, osteoporosis, gingivitis and undesired hematopoietic stem cells release.

\* \* \* \* \*